United States Patent [19]
Johnson

[11] Patent Number: 4,826,485
[45] Date of Patent: May 2, 1989

[54] DEVICE FOR GUIDING TUBINGS

[75] Inventor: Theodore D. Johnson, Largo, Fla.

[73] Assignee: Concept Polymer Technologies, Inc., Clearwater, Fla.

[21] Appl. No.: 629,819

[22] Filed: Jul. 11, 1984

[51] Int. Cl.⁴ ............................................. A61M 25/00
[52] U.S. Cl. ..................................................... 604/170
[58] Field of Search ................ 128/768, 772; 604/170, 604/270, 282

[56] References Cited
U.S. PATENT DOCUMENTS 3,128,769 4/1964 Scislowicz .................. 604/170
4,137,916 2/1979 Killman et al. .............. 604/170
4,388,076 6/1983 Waters ........................ 604/170

Primary Examiner—C. Fred Rosenbaum
Attorney, Agent, or Firm—Sherman & Shalloway

[57] ABSTRACT

A stylet comprising a flexible stiffening means for guiding and positioning a flexible tubing, the stiffening means having distal and proximal ends, the distal end being insertable into the flexible tubing; and a connector having an off-centered through bore to provide thick and thin wall portions, the proximal end of the stiffening means being embedded in the thick wall portion.

22 Claims, 4 Drawing Sheets

– 1 –

DEVICE FOR GUIDING TUBINGS

BACKGROUND OF THE INVENTION

1. Field of the Invention

This invention relates to a device for guiding flexible tubings, more specifically enteral feeding tubings.

2. Description of the Prior Art

The use of a stiffening means or stylet, within a flexible tubing to stiffen the tubing so as to introduce the tubing into the correct location in a patient is known. To determine whether the tip of the tubing is properly positioned, the physician usually uses X-ray or other methods such as aspiration of gastric contents for analysis and identification. It is conventional to remove the stylet after the tubing has been inserted into the patient. In the event that it is subsequently found that the tip of the tubing has not been properly positioned, the stylet must be reintroduced into the tubing in the patient. Such a procedure is risky since there is the possibility that the end of the stylet may protrude the tubing and puncture soft gastrointestinal and respiratory tissues. Alternatively, the tube may be removed from the patient, with the stylet being re-inserted into the tubing outside the patient. Such a procedure induces discomfort in the patient and also requires more time, particularly if the procedure has to be repeated before the tube is lodged in the proper position.

In U.S. Pat. No. 4,388,076, there is provided an enteral feeding device wherein the stylet comprises a hollow stylet connector and a flexible wire having one end formed into a hook and inserted into one end of the connector plug. According to the patentee, it is not necessary to remove the stylet after positioning the tubing since the stylet does not hinder access to the proximate end of the enteric tubing. However, the proximate end of this stylet is merely placed within the connector. As a result the hook formed into the end of the wire may become exposed and cause harm not only to the patient but also to the medical staff caring for him. Furthermore, since the stylet is placed within the inner diameter of the connector this means that the stylet may impede the flow of material through the connector.

The present invention provides a stylet wherein there are no exposed sharp points and the stylet is placed off-centered so that it does not obstruct the flow of material through the connector.

SUMMARY OF THE INVENTION

This invention provides a device for guiding flexible tubings, which device comprises an elongated stiffening means for positioning and guiding the flexible tubing, the stiffening means having a distal end insertable into the tubing and a proximal end; and a connector having an off-centered through bore forming a thick wall portion and thin wall portion, the proximal end of the stiffening means being embedded in the thick wall portion.

DETAILED DESCRIPTION OF THE INVENTION

The present invention provides a device for guiding flexible tubing, i.e. a stylet. The stylet can be used in conjunction with enteral feeding tubing and other tubings having medical applications. The stylet comprises a connector having embedded therein one end of a stiffening means. The present stylet is so constructed that there are no sharp or pointed edges which may cause harm to the patient. Furthermore, flow through the connector in the present device is not impeded by the stiffening means.

Figure 1:
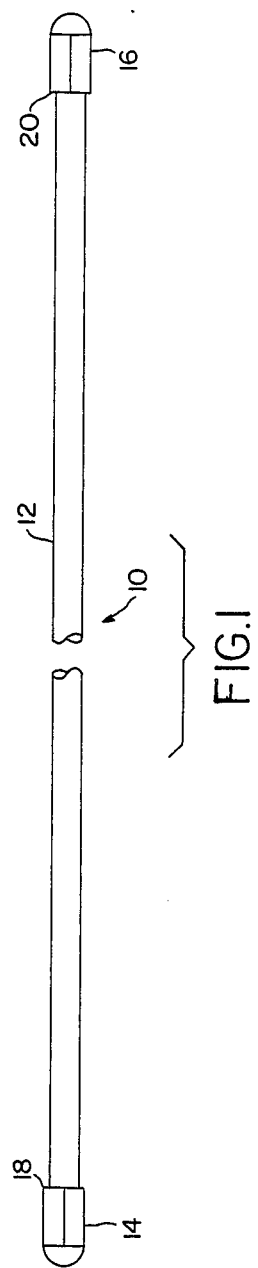
FIG. 1 illustrates the stiffening means.

With reference to the drawings, FIG. 1 shows the construction of the stiffening means 10 used in forming the present stylet. Stiffening means 10 comprises cable 12 which may be made of metal or a stiff polymeric material and enlarged portions 14 and 16 attached to the ends thereof. Cable 12 is formed by twisting a plurality of thinner strands of wire or polymeric materials, typically three. Enlarged portions 14 and 16 are joined to the ends of cable 12 by swaging, welding or other conventional method. As shown in FIG. 1, enlarged portions 12 and 14 are in the shape of a bullet, i.e. a cylinder having one end rounded to eliminate sharp corners or edges. It is understood that the enlarged portions are not limited to such shape. Any configuration can be used, as long as there are no sharp points or edges. As shown in FIG. 1, enlarged portions 14 and 16 have a diameter which is greater than that of cable 12 to provide shoulder portions 18 and 20 which prevent cable 12 from being pulled out of the connector after cable 12 has been embedded therein. Cable 12 and enlarged portions 14 and 16 preferably are made of stainless steel whereas the cable between enlarged portions 14 and 16 preferably is coated with an inert polymeric material such as medical grade Teflon. Typically, uncoated cable 12 has a diameter of from about 0.026 to 0.030 inch and a Teflon coating thickness ranging from about 0.002 to 0.004 inch. Enlarged portions 14 and 16 may have a length of from about 0.120 to 0.180 inch and a diameter of from about 0.04 to 0.06 inch.

The connector is provided with an off-centered through bore to provide a thick wall portion and a thin wall portion. One end (proximal) of cable 12 is embedded in the thick wall portion to form the stylet, whereas the other end (distal) is insertable into the flexible tubing to be guided by the stylet.

Figure 2:
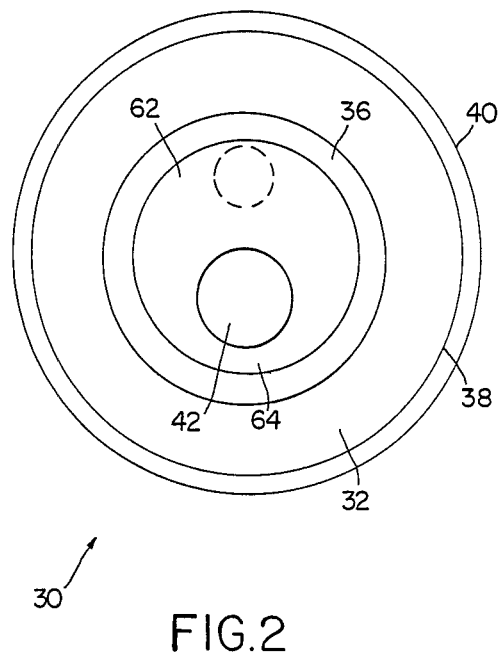
FIG. 2 shows an end view of the connector.
Figure 3:
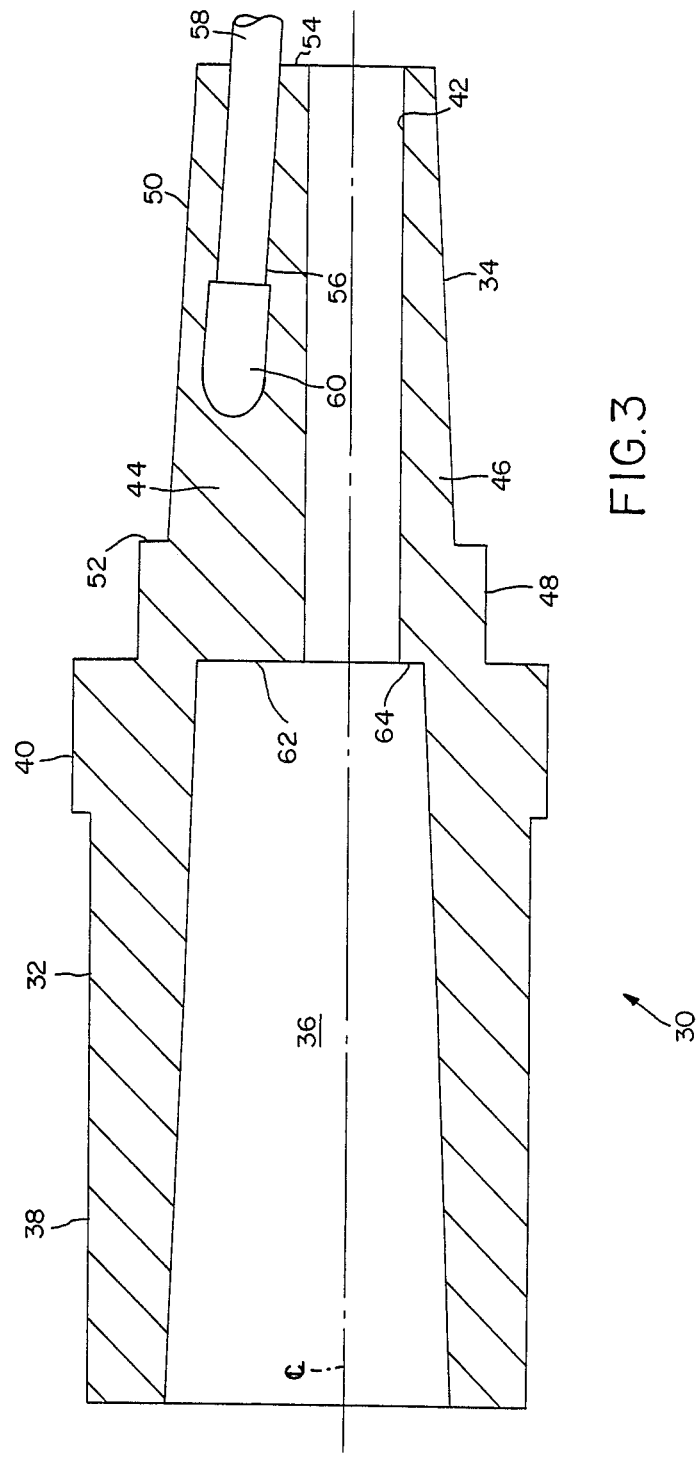
FIG. 3 is a cross sectional view along line A—A of FIG. 2.

FIGS. 2 and 3 show the end view and cross-sectional view of one embodiment of the connector in the present invention, respectively. In this embodiment, connector plug 30 comprises large section 32 and small section 34, the connector being integrally formed. Large section 32 is provided with a central through bore 36. Preferably, bore 36 is tapered from the outer end towards the center at an angle of from about 3° to 4° to facilitate insertion of syringes and the like. Outer wall 38 of large section 32 is preferably provided with flange portion 40 near the center of connector plug 30.

Typically, large section 32 has a length of from about 0.375 to 0.425 inch, a maximum through bore diameter of from about 0.287 to about 0.297 inch. Outer wall 38 has an outside diameter of from about 0.362 to about 0.382 inch whereas flange portion 40 has an outside diameter of from about 0.390 to about 0.416 inch.

Small section 34 of connector 30 is also provided with a through bore 42. However, through bore 42 is off-set from the centerline of small section 34 so as to form a thick wall portion 44 and thin wall portion 46 therein. Embedded in thick wall portion 44 is one end of cable 12 and the enlarged portion 14. As shown in FIG. 3, cable 12 and thick wall portion 44 are co-axial. Cable 12 and enlarged portion 14 can be imbedded in connector 30 by insertion molding. That is to say, cable 12 with enlarged portion 14 attached securely thereto is placed in a molding machine and connector 30 is then formed over enlarged portion 14 by insertion molding. Since insertion molding is well known, a detailed description of this method is omitted. Preferably, exterior wall of small section 34 comprises a constant diameter portion 48 and reduced diameter portion 50 so as to provide shoulder portion 52. Reduced diameter portion 50 has an outside diameter which decreases from the central portion of the connector plug 30 towards the outer end 54 of small section 34.

Typically, small section 34 has a length of from about 0.390 to 0.410 inch. Constant diameter portion 48 has a diameter of from about 0.332 to about 0.342 inch. The taper in the outside diameter of small section 34 ranges from about 3° to 4°. Due to the presence of the off-set in through bore 42, thick shoulder portion 62 and thin shoulder portion 64 are formed. These shoulders are located at about the center of connector plug 30, i.e. large and small sections 32 and 34 are of approximately equal length. As shown in FIG. 3, through bores 36 and 42 are in communication, with through bore 36 being larger in diameter then through bore 42.

Connector 30 is made of a polymeric material, such as polypropylene or polyvinylchloride.

Figure 4:
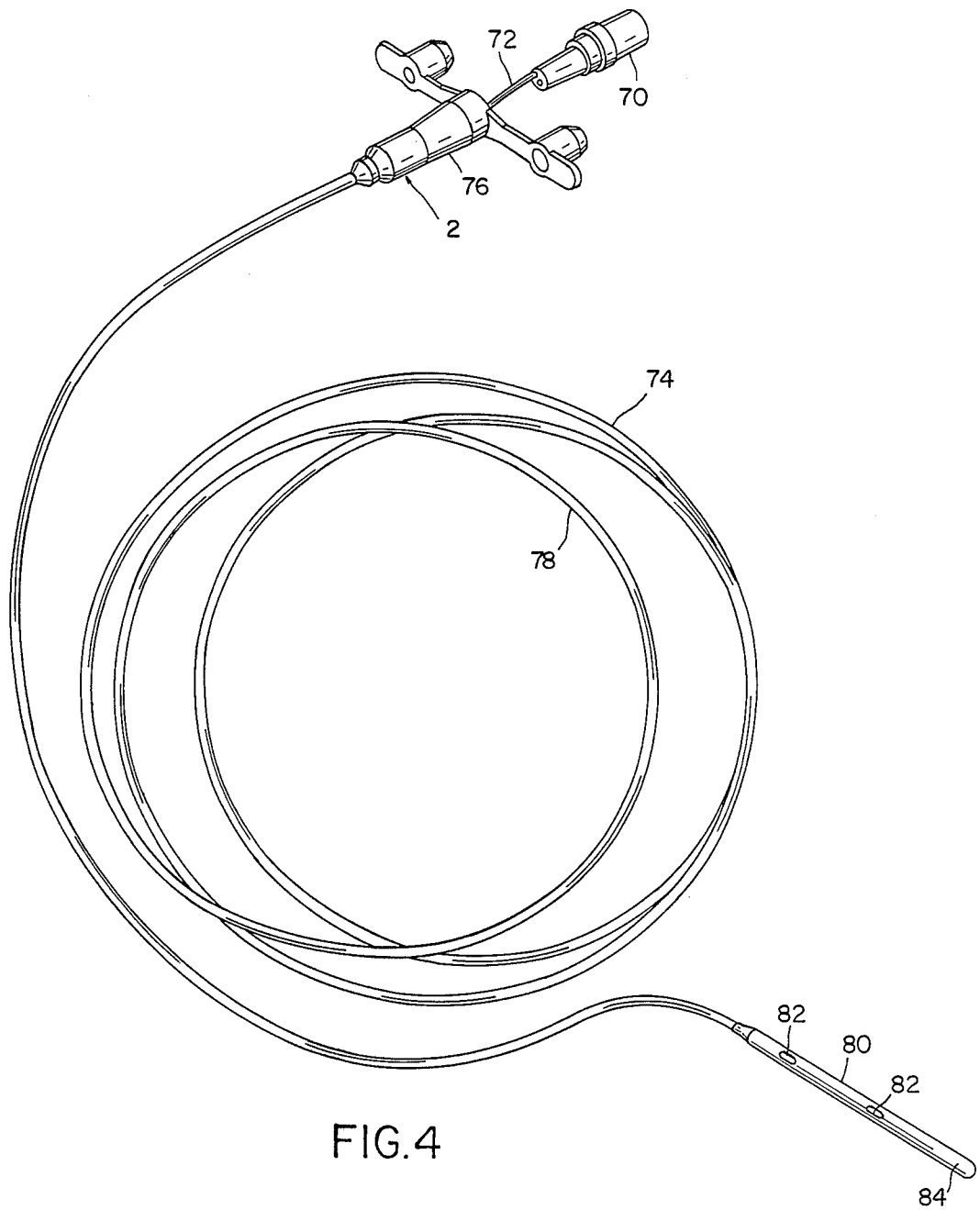
FIG. 4 shows one embodiment of the present device used in conjunction with an enteral feeding tube.

FIG. 4 shows the present stylet in use with an enteral feeding tubing. As shown in FIG. 4, the stylet comprises connector 70 and cable 72. One end of cable 72 is inserted into enteral feeding tube 74. Feeding tube 74 in turn comprises female connector 76 at its proximal end, stem portion 78 and weighted bolus 80 at the distal end. In FIG. 4, the weighted bolus is provided with a plurality of discharge openings 82 which permit flow from within the feeding tube to the exterior thereof. One end of the cable 72 is housed within the tip of weighted bolus 80. The distal end 84 of bolus 80 is closed. However, it is understood that end 84 may be provided with an opening. In addition, the enteral feeding tubing 74 may comprise only a female connector at the proximal end and a stem portion having no weighted bolus connected to the distal end thereof. In such an embodiment the distal end of the stem portion may be closed or open. When the distal end is closed, a plurality of discharge openings are provided adjacent the distal end of the stem portion. With regard to the enteral feeding tube, particularly the composition and construction thereof, applicant's copending and commonly assigned application entitled "Enteral Feeding Tubes", U.S. patent application Ser. No. 559,685, filed Dec. 9, 1983, is incorporated herein by reference.

From the above description, it is clear that the present invention provides a stylet in which the stiffening means is so connected to the connector that no sharp edges or points are exposed. In addition, by offsetting the through bore in the connector and embedding the proximal end of the stiffening means in the connector, the potential risk of having the flow through the connector being obstructed by the stiffening means is completely eliminated.

What is claimed is:

1. A stylet comprising:

elongated stiffening means for guiding and positioning a flexible tubing, said stiffening means having a distal end insertable into said tubing and a proximal end; and a connector having an off-centered through bore to form a thick wall portion and a thin wall portion, said proximal end being embedded in said thick wall portion such that said stiffening means does not present any impediment to flow of material through said through bore.

2. The stylet of claim 1 wherein said stiffening means comprises a cable formed of a metallic material.

3. The stylet of claim 1 wherein the distal end of the stiffening means is connected to a first enlarged portion and the proximal end of the stiffening means is connected to a second enlarged portion.

4. The stylet of claim 3 wherein the cable and the enlarged portions are formed of stainless steel whereas the connector is formed of a polymeric material.

5. A stylet comprising a stiffening cable for guiding and positioning a flexible tubing and having a distal end insertable into said tubing and a connector having a large section and a small section, said large section having a central through bore and said small section having a through bore which is off-centered to provide thick and thin wall portions, said thick wall portion having embedded therein the proximal end of said cable, said through bores being in communication, said cable not presenting any impediment to the flow of material through the bores of the stylet.

6. The device of claim 5 wherein each of the ends of said cable is connected to a different enlarged portion.

7. The device of claim 6 wherein said cable and said enlarged portions are formed of stainless steel.

8. The device of claim 5 wherein said connector is formed of a polymeric material.

9. An enteric feeding device comprising a flexible tubing having an open proximal end, a closed distal end and at least one discharge opening adjacent to said distal end;

a flexible stiffening means having proximal and distal ends, said distal end being insertable into said flexible tubing; and a connector having an off-centered through bore to provide thick and thin wall portions, said thick wall portion having embedded therein the proximal end of said stiffening means, whereby the stiffening means does not present any impediment to flow of material through said through bore.

10. The feeding device of claim 9 wherein each of the ends of said cable is connected to an enlarged portion.

11. The feeding device of claim 10 wherein said cable and enlarged portions are formed of stainless steel.

12. The feeding device of claim 11 wherein said connector and said flexible tubing are formed of a polymeric material.

13. The stylet of claim 1 wherein said stiffening means comprises a cable formed of a stiff polymeric material.

14. The stylet of claim 1 wherein the proximal end of the stiffening means is embedded in said thick wall portion through an opening in the distal end of said thick wall portion.

15. The stylet of claim 3 wherein the second enlarged portion and the immediately adjacent section of the stiffening means are embedded in axial alignment with and in said thick wall portion.

16. The stylet of claim 3 wherein the second enlarged portion and immediately adjacent section of the stiffening means are insertion molded into the thick wall portion.

17. the stylet of claim 5 wherein the proximal end of the stiffening cable is embedded in the thick wall portion through an opening in the distal end of the thick wall portion.

18. The stylet of claim 6 wherein one enlarged portion is embedded in the thick wall portion together with the immediately adjacent section of the stiffening cable said embedded portion and adjacent section being in axial alignment with said thick wall portion.

19. The stylet of claim 5 wherein the proximal end of the stiffening cable which is embedded in the thick wall portion is enlarged and wherein said enlarged end and the section of the stiffening cable immediately adjacent said enlarged end are insertion molded into the thick wall portion.

20. The enteric feeding device of claim 9 wherein the proximal end of the stiffening means is embedded in said thick wall portion through an opening in the distal end of said thick wall portion.

21. The enteric feeding device of claim 10 wherein one enlarged portion is embedded in the thick wall portion together with the immediately adjacent section of the stiffening cable said embedded portion and adjacent section being in axial alignment with said thick wall portion.

22. The enteric feeding device of claim 9 wherein the proximal end of the stiffening means which is embedded in the thick wall portion is enlarged and wherein said enlarged end and the section of the stiffening means immediately adjacent said enlarged end are insertion molded into the thick wall portion.

* * * * *